US008241485B2

(12) United States Patent (10) Patent No.: US 8,241,485 B2
Forrow et al. (45) Date of Patent: *Aug. 14, 2012

(54) BIOSENSOR ELECTRODE MEDIATORS FOR REGENERATION OF COFACTORS

(75) Inventors: Nigel J. Forrow, Abingdon (GB);
Gurdial S. Sanghera, Newton, MA (US); Jared L. Watkin, Abingdon (GB);
Stephan Walters, Edgebaston (GB)

(73) Assignee: Abbott Laboratories, Alameda, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 12/242,744

(22) Filed: Sep. 30, 2008

(65) Prior Publication Data

US 2009/0090624 A1 Apr. 9, 2009

Related U.S. Application Data

(63) Continuation of application No. 10/832,408, filed on Apr. 26, 2004, now Pat. No. 7,504,019, which is a continuation of application No. 09/529,617, filed as application No. PCT/US98/21815 on Oct. 16, 1998, now Pat. No. 6,736,957.

(60) Provisional application No. 60/061,982, filed on Oct. 16, 1997.

(51) Int. Cl.
*G01N 27/327* (2006.01)
(52) U.S. Cl. ............................... 205/777.5; 204/403.14
(58) Field of Classification Search ............. 204/403.01, 204/403.02, 403.12, 403.14; 205/777.5
See application file for complete search history.

(56) References Cited

U.S. PATENT DOCUMENTS

| | | | |
|---|---|---|---|
| 4,490,464 A | 12/1984 | Gorton et al. | |
| 4,654,127 A * | 3/1987 | Baker et al. | 205/792 |
| 4,758,323 A | 7/1988 | Davis et al. | |
| 4,946,562 A * | 8/1990 | Guruswamy | 205/792 |
| 5,096,669 A * | 3/1992 | Lauks et al. | 204/403.02 |
| 5,120,420 A | 6/1992 | Nankai et al. | |
| 5,126,034 A | 6/1992 | Carter et al. | |
| 5,212,622 A | 5/1993 | MacFarlane et al. | |
| 5,266,179 A | 11/1993 | Nankai et al. | |
| 5,512,159 A | 4/1996 | Yoshioka et al. | |
| 5,582,697 A * | 12/1996 | Ikeda et al. | 205/777.5 |
| 5,628,890 A | 5/1997 | Carter et al. | |

(Continued)

FOREIGN PATENT DOCUMENTS

EP 0 125 867 11/1984

(Continued)

OTHER PUBLICATIONS

Carlson, et al., "Mechanism of the Oxidation of NADH by Quinones. Energetic of One-Electron and Hydride Routes", Journal of American Chemical Society, vol. 107, pp. 479-485 (1985).

(Continued)

*Primary Examiner* — Kaj K Olsen
(74) *Attorney, Agent, or Firm* — Edward J. Baba; Khin K. Chin; Bozicevic, Field & Francis LLP

(57) ABSTRACT

The present invention is based on the discovery of NAD+ and NADP+ mediator compounds that do not bind irreversibly to thiol groups in the active sites of intracellular dehydrogenase enzymes. Such mediator compounds avoid a common mode of enzyme inhibition. The mediators can therefore increase the stability and reliability of the electrical response in amperometric electrodes constructed from NAD- or NADP-dependent enzymes.

18 Claims, 8 Drawing Sheets

U.S. PATENT DOCUMENTS

| | | | |
|---|---|---|---|
| 5,651,869 | A | 7/1997 | Yoshioka et al. |
| 5,705,045 | A | 1/1998 | Park |
| 2002/0092612 | A1* | 7/2002 | Davies et al. ............... 156/292 |
| 2004/0031682 | A1* | 2/2004 | Wilsey ................. 204/403.01 |

FOREIGN PATENT DOCUMENTS

| | | |
|---|---|---|
| EP | 0732406 | 9/1996 |
| EP | 0 794 429 | 9/1997 |
| GB | 2 188 728 | 10/1987 |
| JP | 7248310 | 9/1995 |
| JP | 07 209 243 | 11/1995 |
| JP | 8094573 | 4/1996 |
| JP | 8334489 | 12/1996 |
| JP | 9145665 | 6/1997 |

OTHER PUBLICATIONS

Eckert, et al., "Some electrochemical and chemical properties of methoxatin and analogous quinoquinones", Proc. Natl. Acad. Sci. USA, vol. 79; pp. 2533-2536 (1982).

Eckert, et al., "Chemical Properties of Phenanthrolinequinones and the Mechanism of Amine Oxidation by o-Wuinones of Medium Redox Potentials", Journal of American Chemical Society, vol. 105, pp. 4431-4441 (1983).

Geng, et al. "Amperometric biosensors based on dehydrogenase/NAD and heterocyclic quinones", Biosensors and Bioelectronics, vol. 11, No. 12, pp. 1267-1275 (1996).

Gillard, et al., "Optically Active Co-ordination Compounds. Part XX. Reactions of 1, 10-Phenanthroline coordinated to Cobalt (III)", Journal of the Chemical Society, A., pp. 1447-1451 (1970).

Goss, et al., "Spectral, Electrochemical, and Electrocatalytic Properties of 1, 10-Phenanthroline-5,6-dione Complexes of Transition Metals", Inorganic Chemistry, vol. 24, pp. 4263-4267 (1985).

Mullins, et al., "Preparation of some new intercalating europium(III) sensitizers", J. Chem. Soc., Perkin Trans. vol. 1, pp. 75-81 (1996).

Surrey, "Pyocyanine", Organic Synthesis, vol. 3, Ed. E.C. Horning, Wiley, New York, pp. 753-756.

Yosioka, Yakugaku Zasshi, "Studies of Phenazines. III. Wohl-Aue Reactions of m-Nitroanisole and m-Anisidine", vol. 73, pp. 23-25 (1953).

Batchelor, et al., "Amperometric Assay for the Ketone Body 3-Hydroxybutrate", Anal. Chim. Acta., 221, 1989, pp. 289-294.

Itoh et al., Chemistry Letters, vol. 8, pp. 1583-1586, 1992.

Hedenmo et al, Analyst, 1996, vol. 121, pp. 1891-1895.

Hilt et al, Chemistry A European Journal, vol. 3, pp. 79-88, 1997.

Bard and Faulkner, Electrochemical Methods, Fundamentals and Applications, John Wiley & Sons, 1980, pp. 22-26.

Wikipedia entry for beta-hydroxybutyrate, date unknown. (892 Form, May 27, 2010, Re: U.S. Appl. No. 11/849,790).

Wu et al, Analytical Chemistry 1996, 68, pp. 3688-3696.

European Search Report for EP Application No. 10182725.1, dated May 31, 2011.

* cited by examiner

FORMULATION WITH BINDER AND FILLER (PRESENT INVENTION)

PEO FORMULATION (GENG PAPER)

BIOSENSOR ELECTRODE MEDIATORS FOR REGENERATION OF COFACTORS

This application is a continuation of U.S. application Ser. No. 10/832,408, filed Apr. 26, 2004, now U.S. Pat. No. 7,504,019, which is a continuation of application Ser. No. 09/529,617, filed Jun. 7, 2000, now U.S. Pat. No. 6,736,957, which claims priority from PCT/US98/21815, filed on Oct. 16, 1998, which claims priority from U.S. Application Ser. No. 60/061,982, filed Oct. 16, 1997, all of which are incorporated by reference.

BACKGROUND OF THE INVENTION

The invention is in the general field of electrodes for amperometric biosensors. More specifically, the invention is in the field of compounds for use as mediators for the recycling of cofactors used in these electrodes.

NAD- and NADP-dependent enzymes are of great interest insofar as many have substrates of clinical value, such as glucose, D-3-hydroxybutyrate, lactate, ethanol, and cholesterol. Amperometric electrodes for detection of these substrates and other analytes can be designed by incorporating this class of enzymes and establishing electrical communication with the electrode via the mediated oxidation of the reduced cofactors NADH and NADPH.

NAD- and NADP-dependent enzymes are generally intracellular oxidoreductases (EC 1.x.x.x). The oxidoreductases are further classified according to the identity of the donor group of a substrate upon which they act. For example, oxidoreductases acting on a CH—OH group within a substrate are classified as EC 1.1.x.x whereas those acting on an aldehyde or keto-group of a substrate are classified as EC 1.2.x.x. Some important analytes (e.g., glucose, D-3-hydroxybutyrate, lactate, ethanol, and cholesterol) are substrates of the EC 1.1.x.x enzymes.

The category of oxidoreductases is also broken down according to the type of acceptor utilized by the enzyme. The enzymes of relevance to the present invention have $NAD^+$ or $NADP^+$ as acceptors, and are classified as EC 1.x.1.x. These enzymes generally possess sulfhydryl groups within their active sites and hence can be irreversibly inhibited by thiol-reactive reagents such as iodoacetate. An irreversible inhibitor forms a stable compound, often through the formation of a covalent bond with a particular amino acid residue (e.g., cysteine, or Cys) that is essential for enzymatic activity. For example, glyceraldehyde-3-P dehydrogenase (EC 1.2.1.9) is stoichiometrically alkylated by iodoacetate at $Cys_{149}$ with concomitant loss of catalytic activity. In addition, the enzymes glucose dehydrogenase, D-3-hydroxybutyrate dehydrogenase (HBDH), and lactate dehydrogenase are known to be irreversibly inhibited by thiol reagents. Thus, in seeking to develop stable biosensors containing NAD- or NADP-dependent dehydrogenases, avoidance of compounds that are reactive toward thiols is imperative, as they can act as enzyme inhibitors.

SUMMARY OF THE INVENTION

The present invention is based on the discovery of $NAD^+$ and $NADP^+$ mediator compounds that do not bind irreversibly to thiol groups in the active sites of intracellular dehydrogenase enzymes. Such mediator compounds avoid a common mode of enzyme inhibition. The mediators can therefore increase the stability and reliability of the electrical response in amperometric electrodes constructed from NAD- or NADP-dependent enzymes. In one embodiment, the invention features a test element for an amperometric biosensor. The element includes an electrode, which has test reagents distributed on it. The test reagents include a nicotinamide cofactor-dependent enzyme, a nicotinamide cofactor, and a mediator compound having one of the formulae:

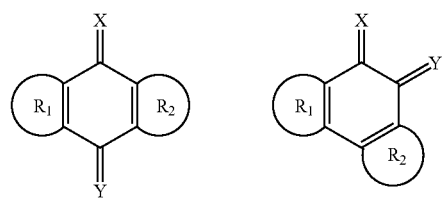

or a metal complex or chelate thereof, where X and Y can independently be oxygen, sulphur, $CR^3R^4$, $NR^3$, or $NR^3R^{4+}$; $R_1$ and $R_2$ can independently be a substituted or unsubstituted aromatic or heteroaromatic group; and $R^3$ and $R^4$ can independently be a hydrogen atom, a hydroxyl group or a substituted or unsubstituted alkyl, aryl, heteroaryl, amino, alkoxyl, or aryloxyl group. In some cases, either X or Y can be the functional group $CZ^1Z^2$ where $Z^1$ and $Z^2$ are electron withdrawing groups.

Any alkyl group, unless otherwise specified, may be linear or branched and may contain up to 12, preferably up to 6, and especially up to 4 carbon atoms. Preferred alkyl groups are methyl, ethyl, propyl and butyl. When an alkyl moiety forms part of another group, for example the alkyl moiety of an alkoxyl group, it is preferred that it contains up to 6, especially to 4, carbon atoms. Preferred alkyl moieties are methyl and ethyl.

An aromatic or aryl group may be any aromatic hydrocarbon group and may contain from 6 to 24, preferably 6 to 18, more preferably 6 to 16, and especially 6 to 14, carbon atoms. Preferred aryl groups include phenyl, naphthyl, anthryl, phenanthryl and pyryl groups especially a phenyl or naphthyl, and particularly a phenyl group. When an aryl moiety forms part of another group, for example the aryl moiety of an aryloxyl group, it is preferred that it is a phenyl, naphthyl, anthryl, phenanthryl or pyryl, especially phenyl or naphthyl, and particularly a phenyl moeity.

A heteroaromatic or hetaryl group may be any aromatic monocyclic or polycyclic ring system, which contains at least one heteroatom. Preferably, a heteroaryl group is a 5 to 18-membered, particularly a 5 to 14-membered, and especially a 5 to 10-membered, aromatic ring system containing at least one heteroatom selected from oxygen, sulphur and nitrogen atoms. 5 and 6-membered heteroaryl groups, especially 6-membered groups, are particularly preferred. Heteroaryl groups containing at least one nitrogen atom are especially preferred. Preferred heteroaryl groups include pyridyl, pyrylium, thiopyrylium, pyrrolyl, furyl, thienyl, indolinyl, isoindolinyl, indolizinyl, imidazolyl, pyridonyl, pyronyl, pyrimidinyl, pyrazinyl, oxazolyl, thiazolyl, purinyl, quinolinyl, isoquinolinyl, quinoxalinyl, pyridazinyl, benzofuranyl, benzoxazolyl and acridinyl groups.

When any of the foregoing substituents are designated as being substituted, the substituent groups which may be present may be any one or more of those customarily employed in the development of compounds for use in electrochemical reactions and/or the modification of such compounds to influence their structure/activity, solubility, stability, mediating ability, formal potential (E°) or other property. Specific examples of such substituents include, for example, halogen atoms, oxo, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, arylsulphinyl, arylsulphonyl, carbamoyl, alkylamido, aryl or aryloxy groups. When any of the foregoing substituents represents or contains an alkyl substituent group, this may be linear or branched and may contain up to 12, preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A halogen atom may be a fluorine, chlorine, bromine or iodine atom and any group which contains a halo moiety, such as a haloalkyl group, may thus contain any one or more of these halogen atoms.

An electron withdrawing group may be any group, which forms a stable methylene group $CZ^1Z^2$. Such electron withdrawing groups may include halogen atoms, nitro, cyano, formyl, alkanoyl, carboxyl and sulphonic acid groups.

Preferably, X and Y are both oxygen atoms.

It is also preferred that $R_1$ and $R_2$ are independently selected from phenyl, naphtuyl, pyridyl and pyrrolyl groups with pyridyl groups being especially preferred. The term "pyridyl group" also includes the N-oxide thereof as well as pyridinium and N-substituted pyridinium groups.

Preferably, $R_1$ and $R_2$ are unsubstituted or substituted only by one or more, preferably one or two, alkyl groups, especially methyl groups. It is especially preferred that $R_1$ and $R_2$ are unsubstituted.

$R_3$ and $R_4$, if present, are preferably independently selected from hydrogen atoms and alkyl groups.

Metal complex and chelates include complexes and chelates with transition metals, especially first-, second-, and third-row transition elements such as ruthenium, chromium, cobalt, iron, nickel and rhenium, with ruthenium being particularly preferred. Other groups such as 4-vinyl-4'-methyl-2,2'-bipridyl (v-bpy) and bipyridyl (bpy) groups may also be included in such complexes and chelates as parts of a complex metal ion. Typically, such complexes and chelates will form as a result of heteroatoms in $R_1$ and $R_2$ coordinating with a metal ion or metal ion complex.

The test reagents can be deposited on the electrode in one or more ink-based layers. The test reagents can be screen-printed onto the working electrode in a single layer.

The element can be an amperometric dry-strip sensor that includes an elongated, electrically insulating carrier having a pair of longitudinal, substantially parallel electrically conducting tracks thereupon, and a pair of electrodes. The electrodes can each be electrically connected to a different one of the tracks; one of the electrodes can be a reference/counter electrode, while another electrode can be a working electrode. The element can also include a dummy electrode. Further, the element can include a membrane positioned to filter samples prior to their introduction onto the electrodes.

The sensor can additionally include a supporting strip of electrically insulating carrier material (e.g., a synthetic polymer such as polyvinyl chloride, or a blend of synthetic polymers).

The mediator compound can be a quinone. Examples of suitable quinones include 1,10-phenanthroline quinone, 1,7-phenanthroline quinone, and 4,7-phenanthroline quinone.

In another embodiment, the invention features an electrode strip for an amperometric sensor having a readout. The strip includes a support adapted for releasable attachment to the readout, a first conductor extending along the support and comprising a conductive element for connection to the readout; a working electrode in contact with the first conductor and positioned to contact a sample mixture; a second conductor extending along the support and comprising a conductive element for connection to the readout; and a reference/counter electrode in contact with the second conductor and positioned to contact the sample and the second conductor. The active electrode of the strip includes a mediator compound having one of the formulae:

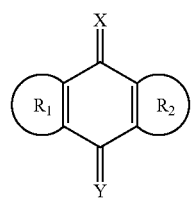 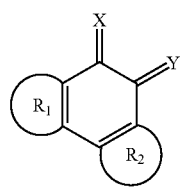

wherein X, Y, $R_1$, and $R_2$ are as previously defined.

Still another embodiment of the invention features a method for mediating electron transfer between an electrode and a nicotinamide cofactor. The method includes the steps of using a mediator compound in the presence of a nicotinamide cofactor-dependent enzyme, where the mediator compound is a quinoid compound that is incapable of binding irreversibly to the thiol groups. The mediator compound can, for example, have reactive unsaturated bonds in adjacent aromatic ring. Suitable mediator compounds include those having the formulae:

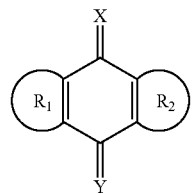 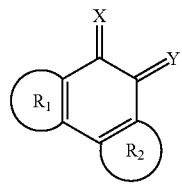

wherein X, Y, $R_1$, and $R_2$ are as previously defined.

For example, the mediator compound can be 1,10-phenanthroline quinone, 1,7-phenanthroline quinone, or 4,7-phenanthroline quinone.

In yet another embodiment, the invention features a printing ink. The ink includes a nicotinamide cofactor-dependent enzyme, a nicotinamide cofactor, and a mediator compound having one of the formulae:

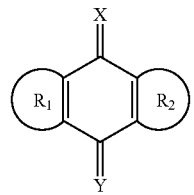 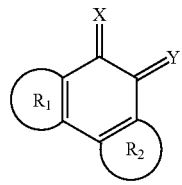

wherein X, Y, $R_1$, and $R_2$ are as previously defined.

For example, the mediator compound can be 1,10-phenanthroline quinone, 1,7-phenanthroline quinone, or 4,7-phenanthroline quinone. The enzyme can be, for example, alcohol dehydrogenase, lactate dehydrogenase, 3-hydroxybutyrate dehydrogenase, glucose-6-phosphate dehydrogenase, glucose dehydrogenase, formaldehyde dehydrogenase, malate dehydrogenase, or 3-hydroxysteroid dehydrogenase.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

An advantage of the new mediators is their non-reactivity with respect to active-site thiol groups in enzymes. This improves the stability and the shelf life of biosensor electrodes to an unexpected degree. Also as a result of this stability, the enzyme and mediator can be incorporated together in a printing ink or dosing solution to facilitate construction of the biosensors. The use of a mediator that is not an irreversible inhibitor of the enzyme will result in the retention of a large proportion of enzyme activity during the biosensor manufacture. NAD- and NADP-dependent dehydrogenase enzymes are generally expensive and labile and improvement of their stability is therefore highly desirable.

Advantageously, the compounds disclosed herein can also be used as mediators to the cofactors NADH and NADPH coupled with a wide range of NAD- or NADP-dependent enzymes; as labels for antigens or antibodies in immunochemical procedures; and in other applications in the field of electrochemistry and bioelectrochemistry. The mediators require low oxidation potentials for re-oxidation following the reaction with NADH or NADPH. This is of particular advantage when testing in whole blood, in which the potential for interference from exogenous electroactive species (e.g., ascorbic acid, uric acid) is particularly high. The low potential can be advantageous because it can obviate the need for a dummy electrode to remove electroactive species in the sample. Also, the oxidized native form of the mediator can decrease the background current that would be present with a reduced mediator.

Other features and advantages of the invention will be apparent from the following detailed description.

DETAILED DESCRIPTION OF THE INVENTION

A class of compounds, selected for their inability to combine irreversibly with thiols, is disclosed for use as NADH or NADPH mediators. The structural, electronic, and steric characteristics of these mediators render them nearly incapable of reacting with thiols. Because these mediators are virtually precluded from binding irreversibly to the active site sulphydryl groups of NAD- and NADP-dependent dehydrogenases, inactivation of the enzyme and consequent loss of biosensor stability is circumvented.

The NADH and NADPH mediators can be used in the manufacture of amperometric enzyme sensors for an analyte, where the analyte is a substrate of an NAD- or NADP-dependent enzyme present in the sensor, such as those of the kind described in EP 125867-A. Accordingly, amperometric enzyme sensors of use in assaying for the presence of an analyte in a sample, especially an aqueous sample, can be made. For example, the sample can be a complex biological sample such as a biological fluid (e.g., whole blood, plasma, or serum) and the analyte can be a naturally occurring metabolite (e.g., glucose, D-3-hydroxybutyrate, ethanol, lactate, or cholesterol) or an introduced substance such as a drug.

Of particular utility for the manufacture of amperometric enzyme sensors, the present invention further provides an ink that includes the NADH and NADPH mediators disclosed herein.

The present invention also includes any precursor, adduct, or reduced (leuco) form of the above mediators that can be converted in situ by oxidation or decomposition to the corresponding active mediators. Such precursors or adducts can include hemiacetals, hemithioacetals, cyclic acetals, metal o-quinone complexes, protonated forms, acetone adducts, etc.

A non-limiting list of enzymes that can be used in conjunction with the new mediators is provided in Table 1.

TABLE 1

| | |
|---|---|
| 1.1.1.1 | Alcohol Dehydrogenase |
| 1.1.1.27 | Lactate Dehydrogenase |
| 1.1.1.31 | 3-Hydroxybutyrate Dehydrogenase |
| 1.1.1.49 | Glucose-6-phosphate Dehydrogenase |
| 1.1.1.47 | Glucose Dehydrogenase |
| 1.2.1.46 | Formaldehyde Dehydrogenase |
| 1.1.1.37 | Malate Dehydrogenase |
| 1.1.1.209 | 3-hydroxysteroid Dehydrogenase I |

Amperometric enzyme sensors adopting the mediators of the present invention generally use a test element, for example, a single-use strip. A disposable test element can carry a working electrode, for example, with the test reagents including the enzyme, the nicotinamide cofactor (i.e., $NAD^+$ or $NADP^+$), the mediators of the present invention for generation of a current indicative of the level of analyte, and a reference/counter electrode. The test reagents can be in one or more ink-based layers associated with the working electrode in the test element. Accordingly, the sensor electrodes can, for example, include an electrode area formed by printing, spraying, or other suitable deposition technique.

Figure 1:
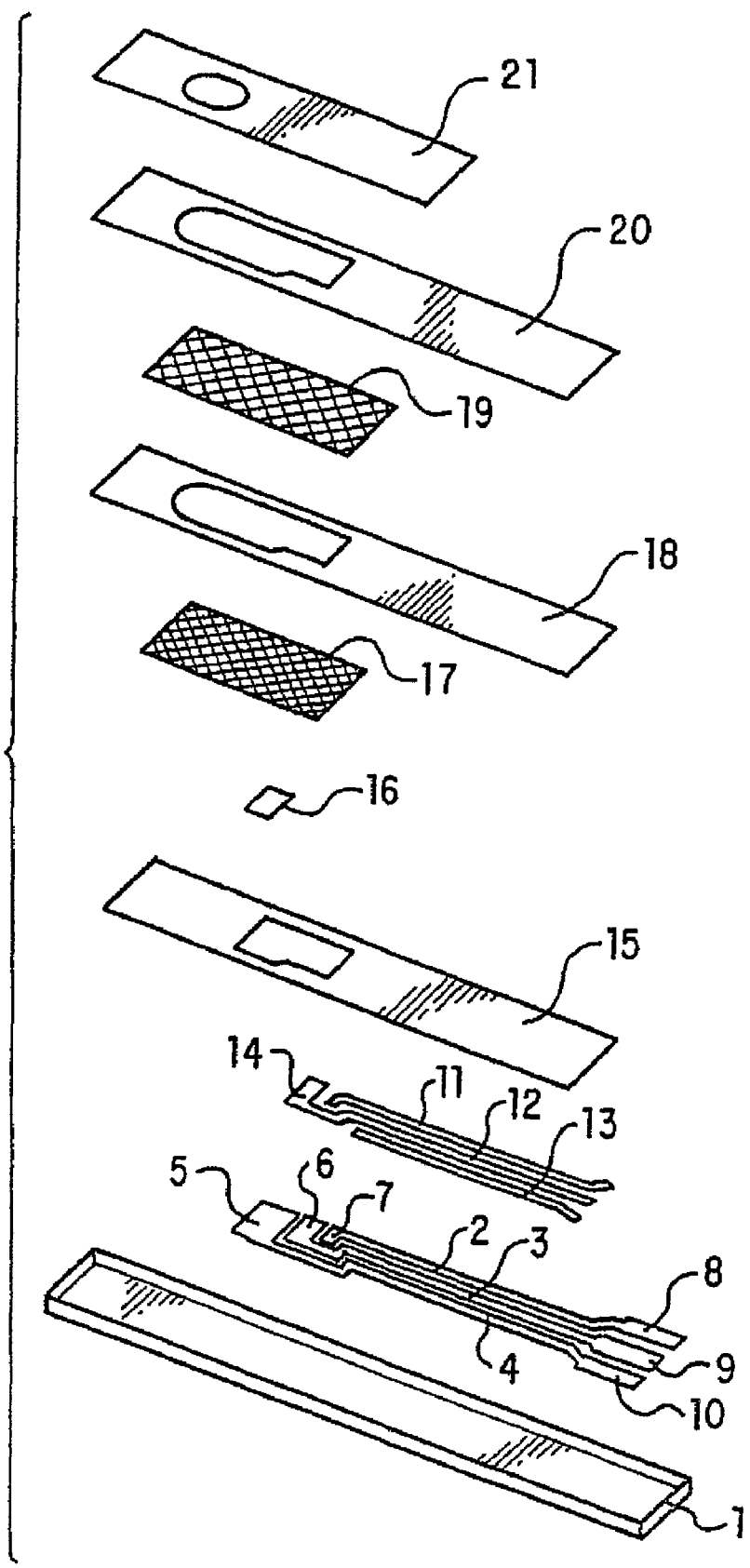
FIG. 1 is an exploded view of an electrode strip according to one embodiment of the invention.
Figure 2:
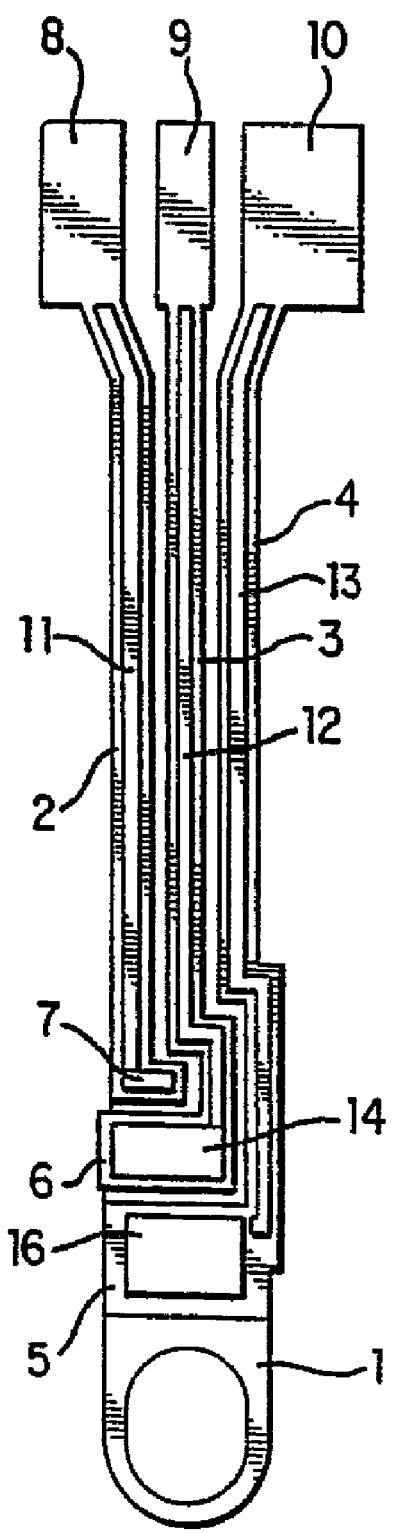
FIG. 2 is a representation of an assembled electrode strip.

Referring to FIGS. 1 and 2, an electrode support 1, typically made of PVC, polycarbonate, or polyester, or a mixture of polymers (e.g., Valox, a mixture of polycarbonate and polyester) supports three printed tracks of electrically conducting carbon ink 2, 3, and 4. The printed tracks define the position of the working electrode 5 onto which the working electrode ink 16 is deposited, the reference/counter electrode 6, the fill indicator electrode 7, and contacts 8, 9, and 10.

The elongated portions of the conductive tracks are respectively overlaid with silver/silver chloride particle tracks 11, 12, and 13 (with the enlarged exposed area 14 of track 12 overlying the reference electrode 6), and further overlaid with a layer of hydrophobic electrically insulating material 15 that leaves exposed only positions of the reference/counter electrode 14, the working electrode 5, the fill indicator electrode 7, and the contact areas 8, 9, and 10. This hydrophobic insulating material serves to prevent short circuits. Because this insulating material is hydrophobic, it can serve to confine the sample to the exposed electrodes. A suitable insulating material is Sericard, commercially available from Sericol, Ltd. (Broadstairs, Kent, UK). Optionally, a first mesh layer 17, a second insulative layer 18, a second mesh layer 19, a third insulative layer 20, and a tape 21 can overlay the hydrophobic insulating material.

Respective ink mixtures can be applied onto a conductive track on a carrier, for example, in close proximity to a reference electrode 14 connected to a second track. In this way, a sensor can be produced, which is capable of functioning with a small sample of blood or other liquid covering the effective electrode area 5. The mixtures are preferably, but not exclusively, applied to the carrier by screen printing.

In general, NAD(P)-dependent dehydrogenases catalyze reactions according to the equation:

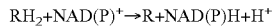

$$RH_2 + NAD(P)^+ \rightarrow R + NAD(P)H + H^+$$

where $RH_2$ represents the substrate (analyte) and R the product. In the process of the forward reaction, $NAD(P)^+$ (i.e., $NAD^+$ or $NADP^+$) is reduced to $NAD(P)H$. Suitable amperometric biosensors provide an electrochemical mediator that can reoxidize $NAD(P)H$, thereby regenerating $NAD(P)^+$. Reoxidation occurs at an electrode to generate a current that is indicative of the concentration of the substrate.

In one embodiment, a dry sensor is provided. The sensor includes an elongated electrically insulating carrier having a pair of longitudinal, substantially parallel, electrically conducting tracks thereupon, each track being provided at the same end with means for electrical connection to a read-out and provided with an electrode, one of the electrodes being the reference/counter electrode and the other being the working electrode, together with test reagents. The sensor can be configured in the form of a supporting strip of electrically insulating carrier material such as a synthetic polymer (e.g., PVC, polycarbonate, or polyester, or a mixture of polymers such as Valox) carrying the two electrodes supported on electrically conductive tracks between its ends. For example, the electrodes can take the form of two rectangular areas side by side on the carrier strip, as shown in FIG. 2 (i.e., electrodes 14 and 16). Such areas can be designed as a target area to be covered by a single drop of sample, such as whole blood, for testing the analyte. If desired, non-rectangular areas (e.g., diamond-shaped, semicircular, circular, or triangular areas) can be employed to provide a target area for optimized contact by a liquid sample.

The carrier includes at least two electrodes, namely a reference/counter electrode and a working electrode. Other electrodes such as a dummy electrode can also be included. These other electrodes can be of similar formulation to the working electrode (i.e., with the associated test reagents), but lacking one or more of the working electrode's active components. A dummy electrode, for example, can provide more reliable results, in that if charge passed at the dummy electrode is subtracted from charge passed at the working electrode, then the resulting charge can be concluded to be due to the reaction of interest.

A membrane can be provided at or above the target to perform a filtration function. For example, a membrane can filter blood cells from a sample before the sample enters the test strip. Examples of commercially available membranes that can be used include Hemasep V, Cytosep, and Hemadyne (Pall Biosupport, Fort Washington, N.Y. 11050). As an alternative, a filtration or cellular separation membrane can be cast in situ. This can be achieved by casting hydrophobic polymers such as cellulose acetate, polyvinyl butyral and polystyrene and/or hydrophilic polymers such as hydroxypropyl cellulose, polyvinylpyrrolidone, polyvinyl alcohol and polyvinyl acetate.

In another embodiment, there is provided a single use disposable electrode strip for attachment to signal readout circuitry of a sensor system. The strip can detect a current representative of an analyte in a liquid mixture. The strip includes an elongated support adapted for releasable attachment to the readout circuitry; a first conductor extending along the support and including a conductive element for connection to the readout circuitry; a working electrode on the strip in contact with the first conductor and positioned to contact the mixture; a second conductor extending along the support, comprising a conductive element for connection to the readout circuitry; and a reference/counter electrode in contact with the second conductive element and positioned to contact the mixture and the second conductor as depicted in FIG. 1.

The working electrode can include a printed layer on the support, and the printed layer itself can include an NAD- or NADP-dependent dehydrogenase enzyme capable of catalyzing a reaction involving a substrate for the enzyme. This layer can also include the corresponding nicotinamide cofactor and a mediator of the present invention capable of transferring electrons between the enzyme-catalyzed reaction and the first conductor via NADH or NADPH, to create a current representative of the activity of both the enzyme and the analyte.

The first conductive element and the active electrode can be spaced apart from the second conductive element and the reference/counter electrode, and the electrodes sized and positioned to present a combined effective area small enough to be completely covered by a drop of blood or other test sample; typically the reaction zone is 5 mm² but can be as large as 25 mm². The test sample completes an electrical circuit across the active electrode and the reference/counter electrode for amperometric detection of the activity of the enzyme.

In a preferred embodiment of the present invention a working electrode is produced by using a formulation which includes not only the enzyme, nicotinamide cofactor and the mediator but also filler and binder ingredients which cause the working electrode to give an increasing monotonic response to concentrations of interest for the analyte being sensed when measured in a kinetic mode in which oxidation and reduction of the mediator both occur during the measurement. The concept is to provide a stable reaction layer on the surface of the working electrode when the sample is applied. This allows the use of mediators which are sparingly soluble in the sample. As the mediator is reduced by reaction with the enzyme, cofactor and analyte, it is retained in close proximity to the electrode surface so that it can be readily reoxidized without significant loss to precipitation. The maintenance of this thin reaction layer also allows the overall analytical reaction to occur in a small volume of the overall sample so in effect what is measured is the flux of analyte from the bulk specimen to this reaction layer.

This reaction layer needs to remain stable for at least the time to conduct a reproducible kinetic measurement. Typical times for such a measurement range between about 5 and 60 seconds, although stability for longer times is preferred. Typically, the disposable electrode strips of interest are mass produced and therefore it is desirable to have a safety margin with regard to any required property to account for the inherent variability in any mass manufacturing process.

The stability of the reaction layer can be improved by a proper combination of fillers and binders. The layer is preferably sufficiently stable to give an approximately linear reproducible response in a kinetic measurement over the concentration range of interest for a given analyte. For instance, for Ketone bodies (measured as hydroxybutyrate) this would be between about 1 and 8 mM while for glucose it would be between about 2 and 40 mM.

The kinetic measurement involves the cycling of the mediator between an oxidized state and a reduced state. The rate of this cycling, which is reflected in the current observed during the course of the test, is dependent upon the concentration of the analyte in the sample. The greater the concentration of the analyte the more enzyme cofactor which is reduced in the course of the enzyme oxidizing the analyte. The mediator in turn becomes reduced in reoxidizing the cofactor and is then reoxidized at the electrode surface. However, because of its very low solubility only a small amount of mediator is immediately available to react with the reduced cofactor. Consequently mediator which reacts with reduced cofactor and is reoxidized at the electrode will then react with further reduced cofactor and this continues through the course of a kinetic measurement. Thus the greater the concentration of the reduced cofactor (reflective of a greater concentration of analyte in the sample) the greater the driving force for the cycling of the mediator and thus the greater the rate of cycling.

In some cases the cofactor may also engage in cycling between an oxidized state and a reduced state during the kinetic measurement. This depends upon whether there is a sufficient quantity of cofactor initially present to convert all the analyte present in the reaction layer. If there is insufficient cofactor initially present as oxidized cofactor is regenerated it promotes the oxidation of any analyte remaining in the reaction layer by becoming reduced again.

However, what is critical is that a given concentration of analyte reproducible results in the production of the same signal in the kinetic test for a particular electrode strip design and that the signal increases monotonically, preferably linearly, with the concentration of the analyte (in other words that the signal be a true function of the analyte concentration) over the concentration range of interest. This allows the manufacturer of the electrode strips to establish a universal calibration for a given lot of electrode strips such that any given signal obtained from a given strip under standard test conditions uniquely correlates to a particular analyte concentration. Thus it is important that within the concentration range of interest there be no uncontrollable variable other than the analyte concentration which would substantially affect the signal.

The signal may be the current observed at a fixed time after the test is initiated or it may be the current integrated over some period occurring some fixed time after the test is initiated (in essence the charge transferred over some such period). The test is conducted by covering the working electrode and a reference/counter electrode with sample and then applying a potential between them. The current which then flows is observed over some time period. The potential may be imposed as soon as the sample covers the electrodes or it may be imposed after a short delay, typically about 3 seconds, to ensure good wetting of the electrodes by the sample. The fixed time until the current or current integration is taken as the signal should be long enough to ensure that the major variable affecting the observed current is the analyte concentration.

The reference electrode/counter electrode may be a classic silver/silver chloride electrode but it may also be identical to the working electrode in construction. In one embodiment the two separate conductive tracks may both be coated with an appropriate formulation of enzyme, cofactor and mediator in a binder and filler containing aqueous vehicle to yield a coating. In those cases in which the coating is non-conductive, e.g. when the filler is a non-conductor, a common coating may overlay both electrodes. When a potential is applied one of the electrodes will function as a reference/counter electrode by absorbing the electrons liberated at the other, working, electrode. The mediator at the reference/counter electrode will simply become reduced as a result of interaction with the electron flow at its electrode.

The reaction layer which yields the desired behavior is obtained by formulating the working electrode with binder and filler ingredients. The object is to allow the sample to interact with the enzyme, cofactor and mediator but to also ensure that these chemically active ingredients remain in the immediate vicinity of the surface of the electrode. The binder ingredient should include materials which readily increase the viscosity of aqueous media and promote the formation of films or layers. Typical of such materials are the polysaccharides such as guar gum, alginate, locust bean gum, carrageenan and xanthan. Also helpful are materials commonly known as film formers such as polyvinyl alcohol (PVA), polyvinyl pyrrole, cellulose acetate, carboxymethyl cellulose and poly(vinyl oxazolidinone). The filler ingredient should be a particulate material which is chemically inert to the oxidation reduction reactions involved in the measurement and insoluble in aqueous media. It may be electrically conductive or non-conductive. Typical materials include carbon, commonly in the form of graphite, titanium dioxide, silica and alumina.

The active electrode may be conveniently produced by formulating the enzyme, cofactor, mediator and binder and filler ingredients into an aqueous vehicle and applying it to the elongated, electrically insulating carrier having conducting tracks. The formulation may be applied by printing such as screen printing or other suitable techniques. The formulation may also include other ingredients such as a buffer to protect the enzyme during processing, a protein stabilizer to protect the enzyme against denaturation and a defoaming agent. These additional ingredients may also have an effect on the properties of the reaction layer.

The working electrode typically has a dry thickness between about 2 and 50 microns preferably between about 10 and 25 microns. The actual dry thickness will to some extent depend upon the application technique used to apply the ingredients which make up the working electrode. For instance thicknesses between about 10 and 25 microns are typical for screen printing.

However, the thickness of the reaction layer is not solely a function of the dry thickness of the working electrode but also depends upon the effect of the sample on the working electrode. In the case of aqueous samples the formulation of the working electrode ingredients will effect the degree of water uptake this layer displays.

The filler typically makes up between about 20 and 30 weight percent of the aqueous vehicle. The amounts of the other ingredients are typically less than about 1 weight percent of the aqueous vehicle and are adjusted empirically to achieve the desired end properties. For instance, the amount of buffer and protein stabilizer are adjusted to achieve the desired degree of residual enzyme activity. In this regard one may use more enzyme and less stabilizer or less enzyme and more stabilizer to achieve the same final level of enzyme activity. The amount of binder and defoaming agent should be adjusted to give suitable viscosities for the method of application with higher viscosities being suitable for screen printing and lower viscosities being suitable for rotogravure printing.

A suitable aqueous ink formulation can be formulated in accordance with Table 2 with the balance being deformer, buffer, enzyme activity enhancers and water to make up 1 gram of formulated ink.

TABLE 2

| | |
|---|---|
| Enzyme (such as Glucose Dehyrogenase or 3-hydroxybutyrate Dehydrogenase) | 200 to 4000 Units |
| Nicotinamide cofactor (such as NAD) | 5 to 30 weight percent |
| Mediator (such as 1,10 phenanthroline quinone) | 0.1 to 1.5 weight percent |
| Filler (such as ultra fine carbon or titania) | 10 to 30 weight percent |
| Binder (such as alginate or guar gum) | 0.01 to 0.5 weight percent |
| Protein stabilizer (such as Trehalose or Bovine Serum Albumin) | 0.01 to 2 weight percent |

The stability of the reaction layer can be readily evaluated using cyclic voltammetry with various time delays. The working electrode formulation is evaluated by exposing it to a sample containing a relatively high concentration of analyte and subjecting it to a steadily increasing potential to a maximum value and then a steadily decreasing potential back to no applied potential. The resulting current increases to a peak value and then drops off as the voltage sweep continues. Such cyclic voltammetry evaluations are conducted after various delay periods after the working electrode is exposed to the sample. The change in peak current with increasingly long delay periods is a measure of the stability of the reaction layer. The more stable the reaction layer the smaller the decrease in peak current.

An evaluation was conducted to compare the stability of a working electrode formulated in accordance with the teachings of the present invention to that of a "working electrode" formulated according to the teachings of Geng et al. at pages 1267 to 1275 of Biosensors and Bioelectronics, Volume II, number 12 (1996). The working electrode representative of the present invention was formulated with about 25 weight percent filler (ultra fine carbon), binder, protein stabilizer and deformer as taught hereinabove and the working electrode representative of Geng was formulated with a high molecular weight poly(ethylene oxide) as described at page 1267 of the Geng article. In each case a potential was applied at a scan rate of 50 millivolt per second up to 400 mV versus a silver/silver chloride reference electrode after exposing the working electrode to a 20 mM aqueous solution of glucose for 3 seconds and 60 seconds. The formulation according to the present invention yields a stable reaction layer in which the peak current after 60 seconds is 60% of that observed after 3 seconds while the formulation according to the Geng article yields an unstable reaction layer in which no peak current is observable after 60 seconds exposure.

Figure 9:
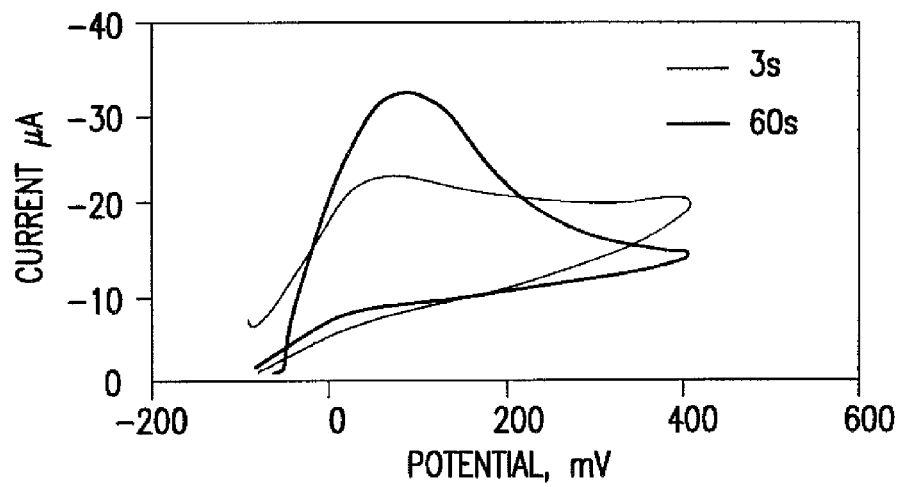
FIG. 9 is a graphical plot of current μA as a function of potential in mV for a working electrode formulated in accordance with the present invention.
Figure 10:
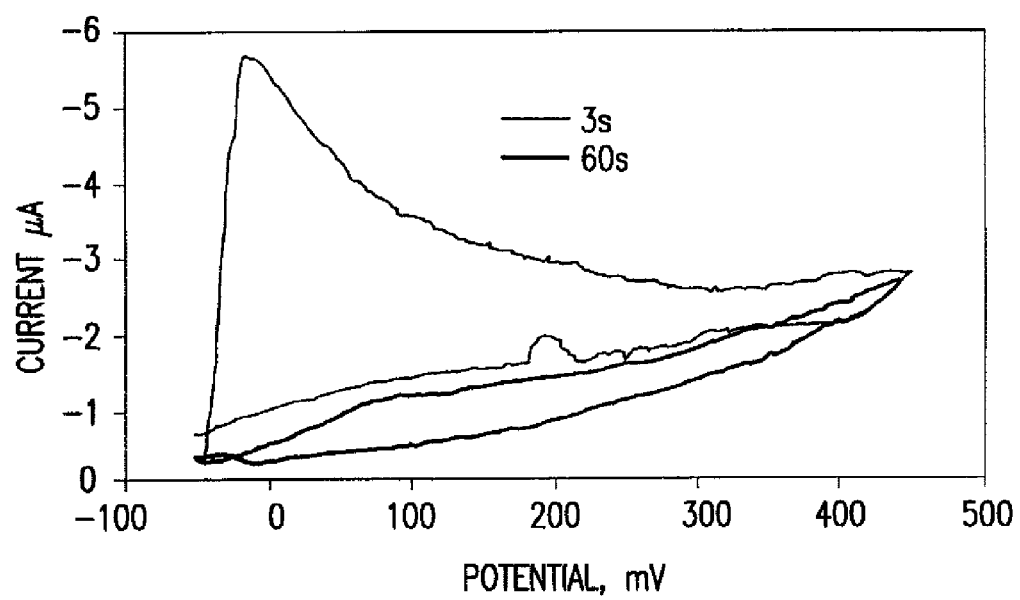
FIG. 10 is a graphical plot of current in μA as a function of potential in mV for a working electrode formulated in accordance with Geng et al.

This is attributed to a dissolution of the electrode with a loss of the reagents to the bulk solution. The respective voltammograms are shown in FIGS. 9 and 10.

The test strips of this invention can detect analytes that are substrates of NAD- or NADP-dependent dehydrogenase enzymes using a mediator selected from the compounds disclosed herein, such as 1,10-PQ.

Test strips according to this invention are intended for use with electronic apparatus and meter systems. These control the progress of the electrochemical reaction (e.g., by maintaining a particular potential at the electrodes), monitor the reaction, and calculate and present the result. A particular feature that is desirable in a meter system for use with test strips of this type is the capability of detecting the wetting of the reaction zone by sample fluid, thus allowing timely initiation of the measurement and reducing the potential for inaccuracies caused by user error. This goal can be achieved by applying a potential to the electrodes of the test strip as soon as the strip is inserted into the meter; this potential can be removed for a short time to allow wetting to be completed before initiation of measurement.

The meter can also feature a means for automatically identifying test strips for measuring different analytes. This can be achieved, for example, when one or more circuit loops are printed on the test strip; each loop can provide a resistance characteristic of the type of strip, as described in U.S. Pat. No. 5,126,034 at column 4, lines 3 to 17. As a further alternative, notches or other shapes might be cut into the proximal end of the test strip; switches or optical detectors in the meter can detect the presence or absence of each notch. Other strip-type recognition techniques include varying the color of the strips and providing the meter with a photodetector capable of distinguishing the range of colors; and providing the strips with barcodes, magnetic strips, or other markings, and providing the meter with a suitable reading arrangement.

In one example of a test strip for large scale production, the strip electrodes have a two-electrode configuration comprising a reference/counter electrode and a working electrode. The carrier can be made from any material that has an electrically insulating surface, including poly (vinyl chloride), polycarbonate, polyester, paper, cardboard, ceramic, ceramic-coated metal, blends of these materials (e.g., a blend of polycarbonate and polyester), or another insulating substance.

A conductive ink is applied to the carrier by a deposition method such as screen printing. This layer forms the contact areas, which allow the meter to interface with the test strip, and provides an electrical circuit between the contacts and the active chemistry occurring on the strip. The ink can be an air-dried, organic-based carbon mixture, for example. Alternative formulations include water-based carbon inks and metal inks such as silver, gold, platinum, and palladium. Other methods of drying or curing the inks include the use of infrared, ultraviolet, and radio-frequency radiation.

A layer forming the reference/counter electrode is printed with an organic solvent-based ink containing a silver/silver chloride mixture. Alternative reference couples include Ag/AgBr, Ag/AgI, and Ag/Ag$_2$O. The print extends to partially cover the middle track of the carbon print where it extends into the reaction zone. It is useful if separate parts of this print are extended to cover parts of other carbon tracks outside the reaction zone, so that the total electrical resistance of each track is reduced.

A layer of dielectric ink can optionally be printed to cover the majority of the printed carbon and silver/silver chloride layers. In this case, two areas are left uncovered, namely the electrical contact areas and the sensing area which will underlie the reactive zone as depicted in FIGS. 1 and 2. This print serves to define the area of the reactive zone, and to protect exposed tracks from short circuit.

For the working electrode, one or more inks are deposited to a precise thickness within a defined area on top of one of the conductive tracks within the reaction zone, to deposit the enzyme, cofactor and a mediator of the present invention. It is convenient to do this by means of screen printing. Other ways of laying down this ink include inkjet printing, volumetric dosing, gravure printing, flexographic printing, and letterpress printing. Optionally, a second partially active ink can be deposited on a second conductive track to form a dummy electrode.

Polysaccharides can optionally be included in the ink formulation. Suitable polysaccharides include guar gum, alginate, locust bean gum, carrageenan and xanthan. The ink can also include a film former; suitable film-forming polymers include polyvinyl alcohol (PVA), polyvinyl pyrrole, cellulose acetate, CMC, and poly(vinyl oxazolidinone). Ink fillers can include titanium dioxide, silica, alumina, or carbon.

The following are illustrative, non-limiting examples of the practice of the invention:

Example 1

Mediators

Meldola's Blue (MB) (Compound 3) was obtained as the hemi-$ZnCl_2$ salt from Polysciences, Inc. 2,6-Dichloroindophenol (DCIP) (Compound 6) and Tris buffer were purchased from Sigma. The phosphate buffered saline (PBS) solution (Dulbecco's formula) was prepared from tablets supplied by ICN Biomedicals, Ltd.

D-3-Hydroxybutyrate dehydrogenase (HBDH; EC 1.1.1.30) from *Pseudomonas* sp. was purchased from Toyobo Co., Ltd. p-Nicotinamide adenine dinucleotide ($NAD^+$) and D,L-3-hydroxybutyric acid were supplied by Boehringer Mannheim.

1,10-Phenanthroline quinone (1,10-PQ) (Compound 7) was prepared according to the method of Gillard et al. (*J. Chem. Soc. A*, 1447-1451, 1970). 1,7-Phenanthroline quinone (1,7-PQ) (Compound 8) was synthesized using the procedure described by Eckert et al. (*Proc. Natl. Acad. Sci. USA*, 79:2533-2536, 1982). 2,9-Dimethyl-1,10-phenanthroline quinone (2,9-$Me_2$-1,10-PQ) (Compound 10) was synthesized as a byproduct of the nitration of neocuproine as disclosed by Mullins et al. (*J. Chem. Soc., Perkin Trans.* 1, 75-81, 1996). 1-Methoxy phenazine methosulphate (1-MeO-PMS) (Compound 5) was prepared via the methylation of 1-methoxy phenazine adapted from the method described by Surrey (*Org. Synth. Coll. Vol.* 3, Ed. E. C. Horning, Wiley, New York, 753-756). 1-Methoxy phenazine was synthesized by a modified Wohl-Aue reaction as reported by Yoshioka (*Yakugaku Zasshi*, 73:23-25, 1953). 4-Methyl-1,2-benzoquinone (4-Me-BQ) (Compound 4) was prepared via oxidation of 4-methyl catechol with o-chloranil according to a general procedure by Carlson et al. (*J. Am. Chem. Soc.*, 107:479-485, 1985). The 1,10-PQ complex [$Ru(bpy)_2$(1,10-PQ)] ($PF_6$)$_2$ (Compound 12) was obtained from [$Ru(bpy)_2Cl_2$] (Strem Chemicals, Inc.) as reported by Goss et al. (*Inorg. Chem.*, 24:4263-4267, 1985).

Preparation of 1-Me-1,10-phenanthrolinium quinone trifluoromethane sulphonate (1-Me-1,10-$PQ^+$) (Compound II)

Methyl trifluoromethane sulphonate (Aldrich) (1.0 ml) was added to a solution of 1,10-PQ (0.50 g, 2.38 mmol) in anhydrous methylene chloride (25 ml) under nitrogen. Immediate precipitation occurred and the resulting mixture was stirred for 24 hours. Filtration followed by washing with methylene chloride afforded 1-Me-1,10-$PQ^+$ (0.65 g, 73%) as a fine yellow powder.

Evaluation of Meldola's Blue and 1,10-PQ as NADH Mediators in Dry Strips

Screen-printed electrodes incorporating 1,10-PQ and MB were produced from an organic carbon ink containing these NAD(P)H mediators at a level of 3.5 mg/g ink. The solid mediators were mixed into a commercial conducting carbon ink (Gwent Electronic Materials).

Figure 3:
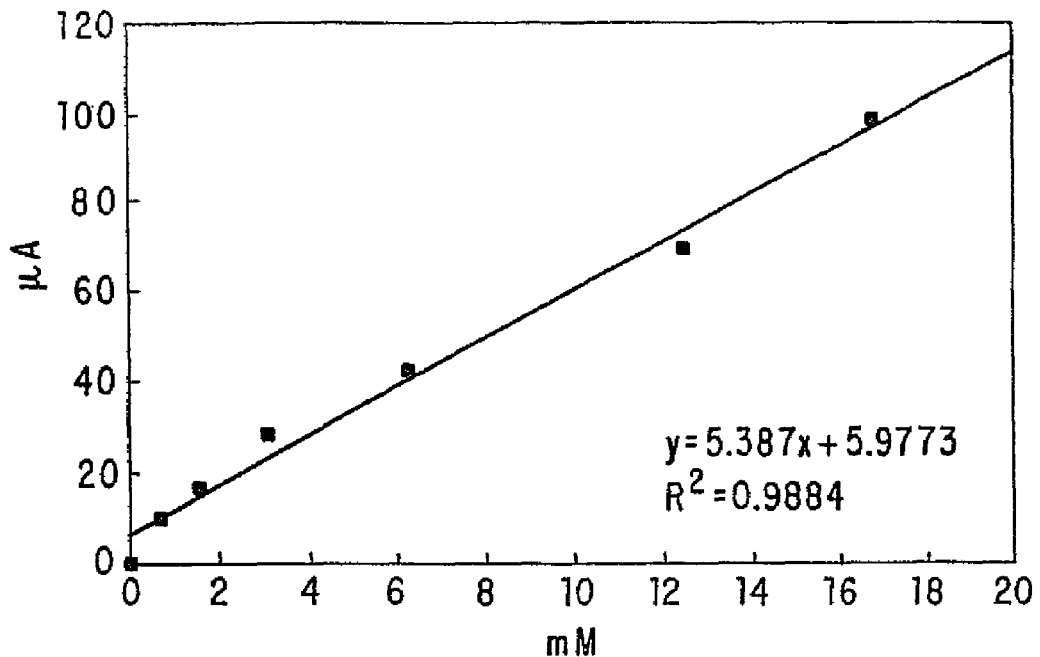
FIG. 3 is a graphical plot of current in μA against NADH concentration in mM for printed electrodes containing 1,10-phenanthroline quinone.
Figure 4:
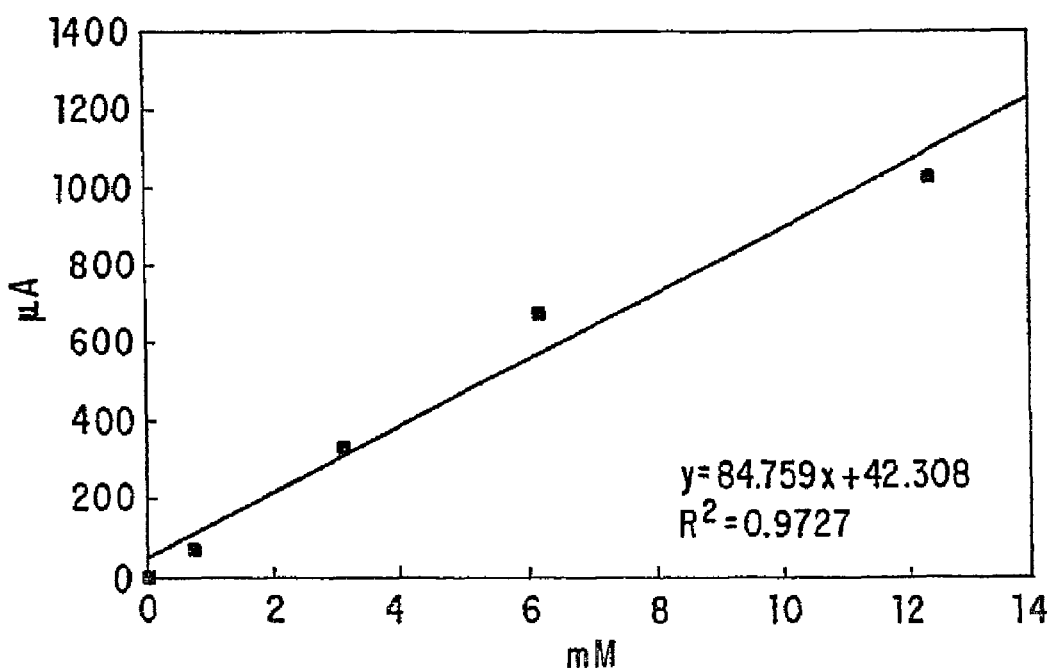
FIG. 4 is a graphical plot of current in μA against NADH concentration in mM for printed electrodes containing Meldola's Blue.

The dose response curve for the electrodes containing 1,10-PQ tested with aqueous NADH solutions (0-16.7 mM) in PBS at a poise potential of +400 mV versus a printed Ag/AgCl reference electrode is shown in FIG. 3. A slope of 0.58 $\mu A\, mM^{-1}$ NADH was recorded. The dose response curve for the electrodes containing MB tested with aqueous NADH solutions (0-12.4 mM) at a poise potential of +100 mV versus a printed Ag/AgCl reference electrode is shown in FIG. 4. An increased slope of 8.48 $\mu A\, mM^{-1}$ NADH was observed.

Assessment of Mediator Inhibition of D-3-Hydroxybutyrate Dehydrogenase

A series of 18 solutions (2.5 ml each) were prepared, each containing 50 U/ml HBDH and 1.29 or 2.58 mg of the following NAD(P)H mediators: MB(3), 4-Me-BQ(4), l-MeO-PMS (5), DCIP(6), 1,10-PQ(7), 1,7-PQ(8), 2,9-$Me_2$-1,10-PQ (10), 1-Me-1,10-$PQ^+$ (11), and [$Ru(bpy)_2$(1,10-PQ)]($PF_6$)$_2$ (12) in Tris buffer (50 mM, pH 8.2). A control solution was also prepared, containing enzyme but no mediator. The solutions were incubated for 0.5 hours at 37.5 C, then assayed (in triplicate) for NADH at 340 nm, using a Sigma Diagnostics D-3-hydroxybutyrate kit. The extent of the interference of the added mediator with the assay rate compared to the control afforded a quantitative measure of the mediator's efficiency as an oxidant of NADH.

The enzyme was then reisolated from the mediator solutions by filtration through a polysulfone membrane (nominal molecular weight cut-off: 30,000) in a microcentrifuge filter (Millipore). The enzyme remaining on the filter was dissolved in Tris buffer (0.2 ml), and the resulting solution was assayed (in triplicate) with the Sigma kit. By comparing the results of the assays before and after filtration, the effect of any covalently and/or irreversibly bound mediator on the enzyme activity could be determined.

The results of the two assays on each solution before and after filtration are collected in Table 3.

TABLE 3

| Mediator (Compound No.) | Assay Rate (absorbance units/min) | | |
|---|---|---|---|
| | control (no mediator) | before filtration | after filtration |
| 1,10-PQ | 0.167 | 0.149 | 0.160 (96%) |
| 1,7-PQ | 0.155 | 0.115 | 0.150 (97%) |
| MB | 0.167 | 0.008 | 0.026 (16%) |
| 4-Me-BQ | 0.170 | 0.005 | 0.007 (4%) |
| 1-MeO-PMS | 0.150 | 0.009 | 0.071 (47%) |
| DCIP | 0.150 | 0.104 | 0.085 (57%) |
| 2,9-Me$_2$-1,10-PQ | 0.197 | 0.189 | n/a |
| 1-Me-1,10-PQ$^+$ | 0.197 | 0.150 | 0.185 (94%) |
| [Ru(bpy)$_2$(1,10-PQ)](PF$_6$)$_2$ | 0.197 | 0.114 | 0.193 (98%) |

Although these results demonstrated that the phenanthroline quinone mediators were relatively inefficient NADH mediators compared to Meldola's Blue and 1-MeO-PMS (i.e., the assay rate "before filtration" was depressed only to a small extent), over 90% of the original enzyme activity for the solutions containing 1,10-PQ, 1,7-PQ, 1-MeO-1,10-PQ, or [Ru(bpy)$_2$(1,10-PQ)](PF$_6$)$_2$ was restored "after filtration." This was not the case for MB, 1-MeO-PMS, DCIP, or 4-Me-BQ. Indeed, the quinone mediator 4-Me-BQ proved to be the most potent inhibitor with only 4% of the original activity remaining "after filtration." Thus, the latter four mediators partially inactivate HBDH while the newly described mediators advantageously had little or no effect on enzyme activity.

Figure 5:
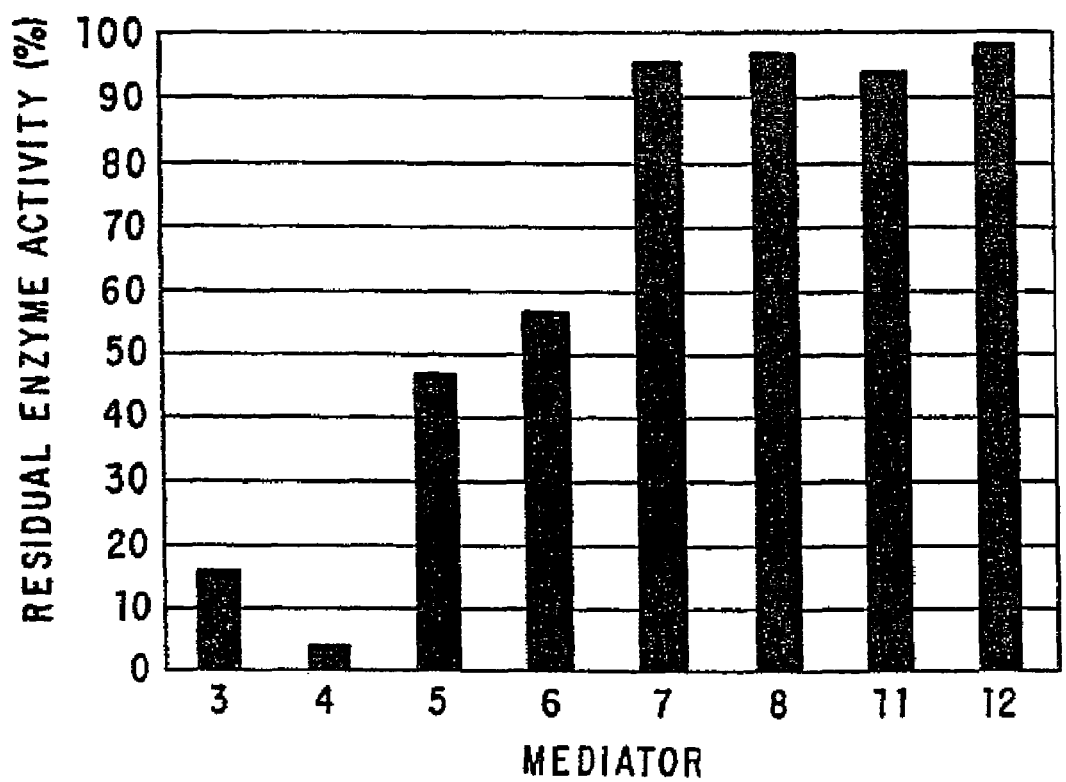
FIG. 5 is a bar chart displaying residual enzyme activity (i.e., as a percentage of the initial activity) after incubation of HBDH with various mediators.

The percentage residual enzyme activities for each mediator are displayed as a bar chart in FIG. 5, which reveals that the mediators of the present invention, represented by black bars, are not strong inhibitors of HBDH. In contrast, MB, 4-Me-BQ, 1-MeO-PMS, and DCIP all irreversibly inhibited HBDH, with concomitant losses in activity ranging from 43 to 96%; these results are represented by grey bars in FIG. 5.

Example 2

Evaluation of Meldola's Blue and 1,10-PQ in Dry Strips Containing HBDH

Screen-printed electrodes were produced from an aqueous carbon ink incorporating 1,10-PQ or MB at a level of 2.4 or 4.3 mg/g ink, respectively, together with the enzyme HBDH (120 units/g ink) and NAD$^+$ (110 mg/g ink). The ink also contained a polysaccharide binder.

Figure 6:
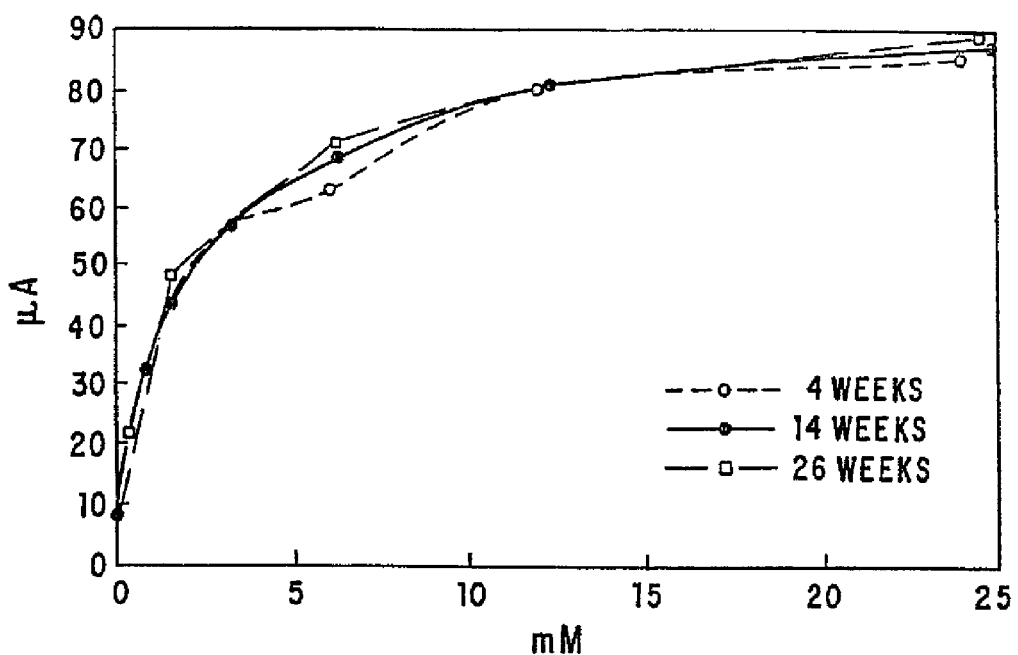
FIG. 6 is a graphical plot of current in μA against D-3-hydroxybutyrate concentration in mM for printed electrodes containing 1,10-phenanthroline quinone, D-3-hydroxybutyrate dehydrogenase and $NAD^+$ tested after 4, 14, and 26 weeks.

The dose response curves for the electrodes containing 1,10-PQ are given in FIG. 6. The electrodes were tested after 4, 14, and 26 weeks of storage (30° C., desiccated) with aqueous D-3-hydroxybutyrate solutions (0-25 mM) in PBS at a poise potential of +400 mV versus a printed Ag/AgCl reference electrode. All three dose responses were non-linear and levelled out with a current of 8.5 µA being recorded at 24 mM D-3-hydroxybutyrate. This demonstrated that the response of the dry electrodes was stable for at least 26 weeks.

Figure 7:
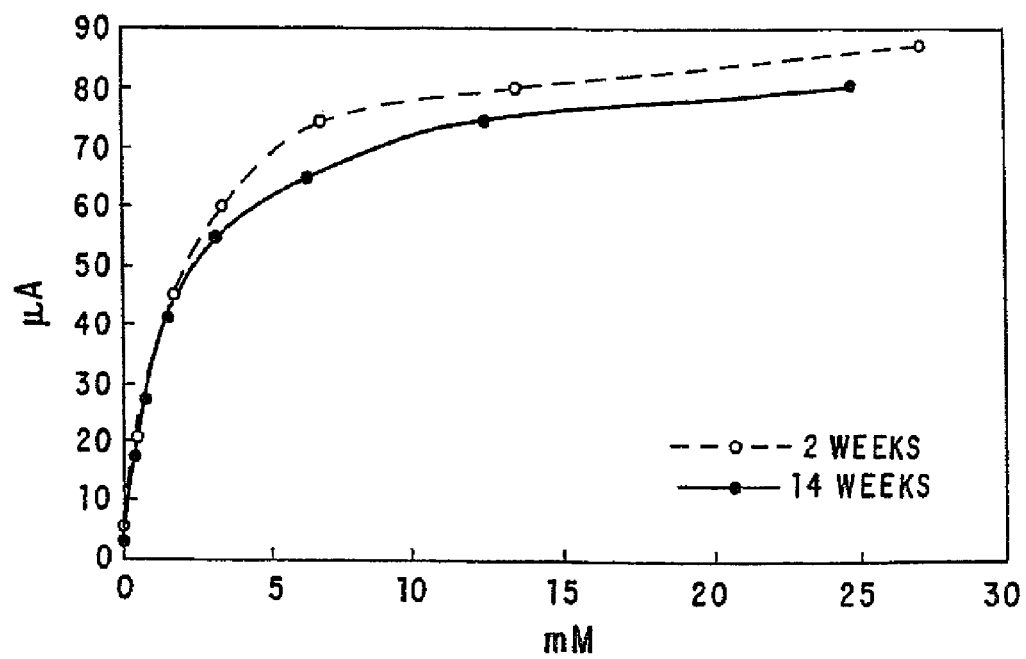
FIG. 7 is a graphical plot of current in μA against D-3-hydroxybutyrate concentration in mM for printed electrodes containing Meldola's Blue, D-3-hydroxybutyrate dehydrogenase, and $NAD^+$ tested after 2 and 14 weeks, respectively.

The dose response curves for the electrodes containing MB are provided in FIG. 7. The electrodes were tested after 2 and 14 weeks storage (30° C., desiccated) with aqueous D-3-hydroxybutyrate solutions (0-28 mM) in PBS at a poise potential of +100 mV versus a printed Ag/AgCl reference electrode. The dose response curves were similar to those in FIG. 4. A current of 8.6 µA was recorded at 24 mM D-3-hydroxybutyrate for these electrodes after 2 weeks storage. This is almost identical to responses obtained from dry strips containing 1,10-PQ.

This result demonstrated that the ability of a compound such as MB to mediate very efficiently with NADH compared to 1,10-PQ is outweighed by the fact that it inhibits HBDH. Furthermore, the stability of the electrode response to D-3-hydroxybutyrate is compromised through the inactivation of HBDH by MB. FIG. 7 shows that the response of these electrodes dropped by an unacceptable margin of approximately 7% after 14 weeks storage.

In summary, biosensor electrodes containing a mediator of the present invention displayed responses which were stable after at least 26 weeks storage. In contrast, those electrodes incorporating a traditional mediator such as MB which is an irreversible enzyme inhibitor exhibited responses which declined after only 14 weeks storage.

Example 3

Evaluation of 1,10-PQ in Dry Strips Containing Glucose Dehydrogenase (GDH)

Screen-printed electrodes were produced from an aqueous carbon ink incorporating 1,10-PQ or MB at a level of 2.4 or 4.3 mg/g ink, respectively, together with the enzyme Glucose dehydrogenase (120 units/g ink) and NAD$^+$ (110 mg/g ink). The ink also contained a polysaccharide binder.

Figure 8:
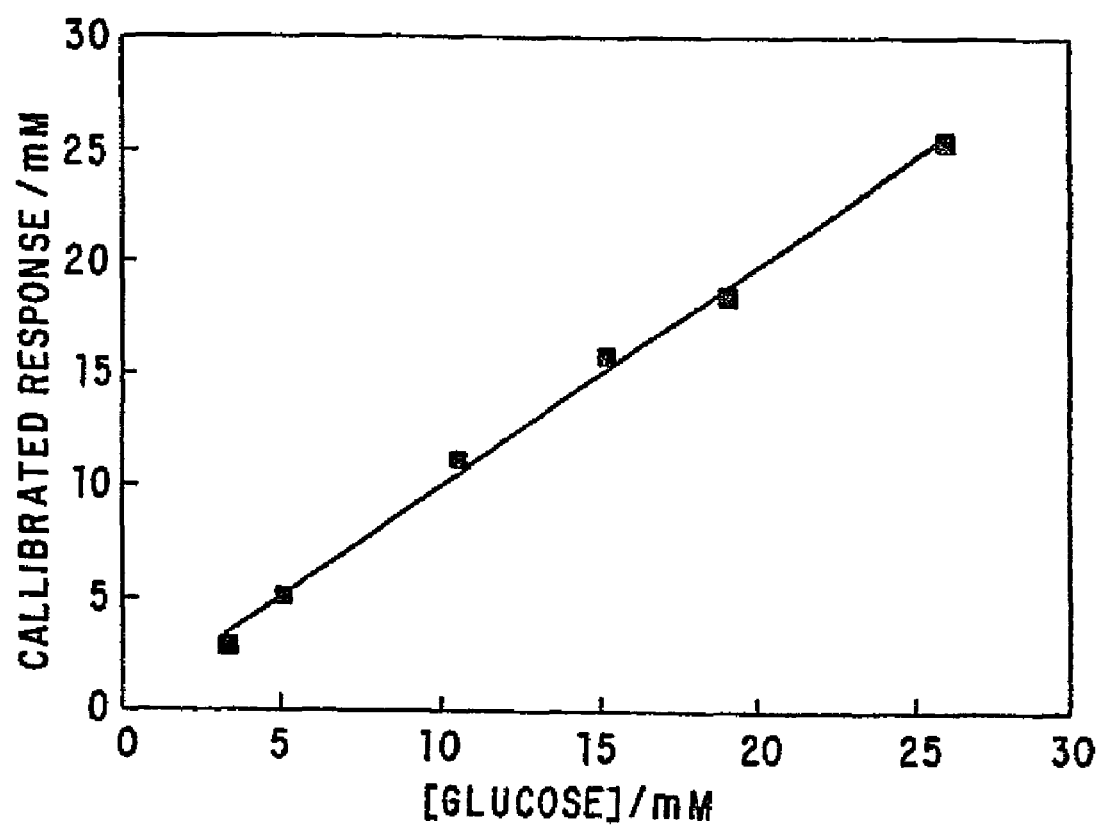
FIG. 8 is a graphical plot of calibrated response to glucose in whole blood for printed electrodes containing 1,10-phenanthroline quinone, glucose dehydrogenase, and $NAD^+$.

The calibrated dose response curve for the electrodes is given in FIG. 8. The electrodes were tested with whole blood containing physiologically relevant concentrations of glucose ranging from 3.3 to 26 mM. A poise potential of +50 mV was maintained against a printed Ag/AgCl electrode. The electrodes produced a linear response over the glucose range. Thus, it was demonstrated that a mediator of the present invention can be used to construct a clinically useful glucose sensor which operates at a particularly low applied potential.

Example 4

Electrode strips were prepared utilizing the construction illustrated in FIGS. 1 and 2 with a silver/silver chloride reference/counter electrode and a working electrode prepared by screen printing a formulation in accordance with Table 2. In one case, the filler was 25 weight percent ultra fine carbon and in the other case the filler was 25 weight percent titania. In both cases the enzyme was Glucose Dehydrogenase (GDH), the cofactor was NAD, the mediator was 1,10-PQ, the binder was guar gum, the protein stabilizer was Bovine serum albumin (BSA) and the buffer was Tris (0.325 weight percent).

Figure 11:
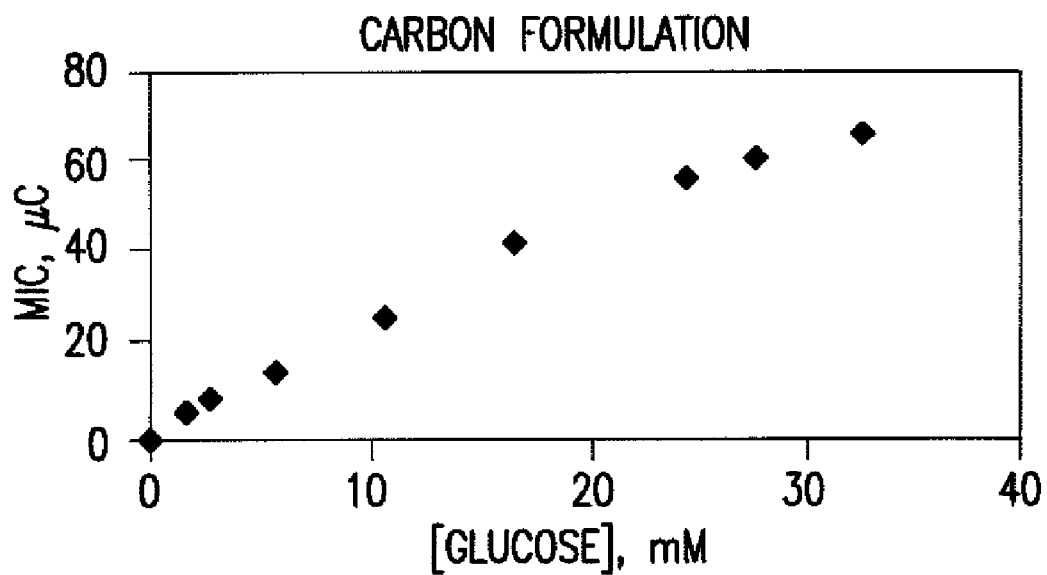
FIG. 11 is a graphical plot of integrated current in μC as a function of the concentration of glucose in mM.
Figure 12:
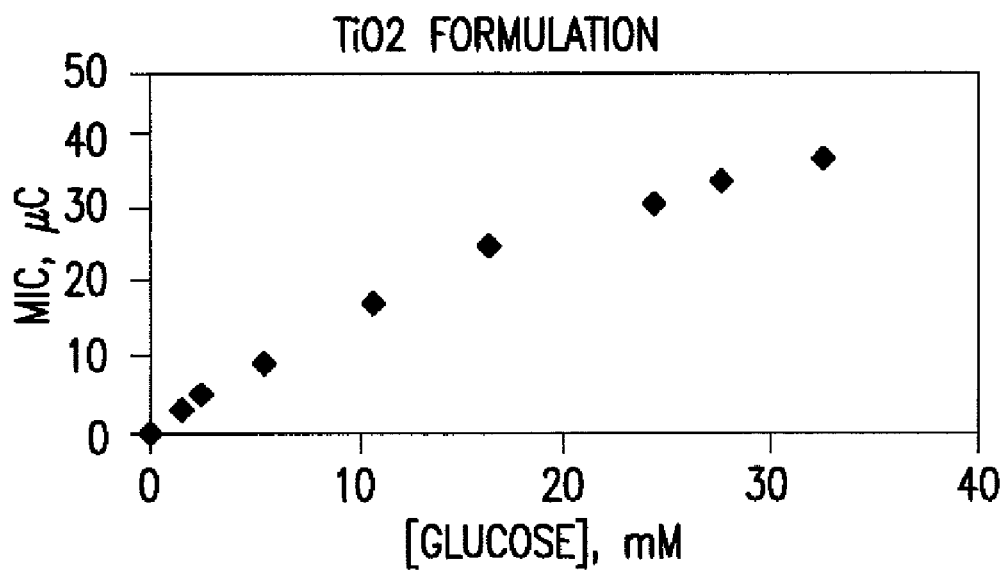
FIG. 12 is a graphical plot of integrated current in μC as a function of the concentration of glucose in mM.

These electrode strips were evaluated by applying a 200 mV potential between the reference/counter electrode and the working electrode while an aqueous glucose solution covered both electrodes. The observed current from 15 to 20 seconds after the application of the potential was integrated and plotted against the glucose contents of the test solutions. The carbon-filled formulation gave a slope of 2.6 microcoulomb per mM of glucose and an X axis intercept of −1 microcoulomb while the titania-filled formulation gave a slope of 1.5 microcoulomb per mM of glucose and an X axis intercept of 0.6 microcoulomb. The plots are shown in FIGS. 11 and 12.

Other Embodiments

It is to be understood that while the invention has been described in conjunction with the detailed description thereof, that the foregoing description is intended to illustrate and not to limit the scope of the invention. Other aspects, advantages, and modifications are within the scope of the invention.

The invention claimed is:

1. A method of determining concentration of an analyte in a sample, the method comprising:
   applying the sample to a biosensor, wherein the biosensor comprises:
   at least two substrates;
   a plurality of electrodes comprising a fill indicator electrode, a working electrode, and a reference or counter/reference electrode; and
   at least one reaction zone comprising an enzyme, a cofactor, and a mediator associated with at least the working electrode, wherein the mediator consists of one of the two following formulae:

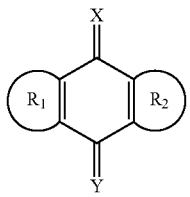 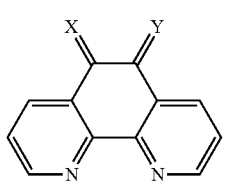

where X and Y can independently be oxygen, sulphur, $CR^3R^4$, $NR^3$, or $NR^3R^{4+}$ or the functional group $CZ^1Z^2$, where $Z^1$ and $Z^2$ are electron withdrawing groups; $R_1$ and $R_2$ can independently be a substituted or unsubstituted aromatic or heteroaromatic group; and $R^3$ and $R^4$ can independently be a hydrogen atom, a hydroxyl group or a substituted or unsubstituted alkyl, aryl, heteroaryl, amino, alkoxyl, or aryloxyl group;
   applying a potential between the working electrode and the reference/counter electrode within 3 seconds of the sample covering the plurality of electrodes; and
   measuring a current between the working electrode and the reference/counter electrode to determine the concentration of the analyte in the sample.

2. The method according to claim 1, wherein the method comprises applying the potential between the working electrode and the reference/counter electrode as soon as the sample covers the plurality of electrodes.

3. The method according to claim 1, wherein the method comprises applying a potential that is 200 mV or less.

4. The method according to claim 3, wherein measuring the current between the working electrode and the counter/reference electrode comprises measuring a signal that increases linearly with the concentration of the analyte in the sample.

5. The method according to claim 1, wherein determining the concentration of the analyte in the sample comprises measuring the current between the working electrode and the reference/counter electrode for about 5 to 60 seconds.

6. The method according to claim 1, wherein the mediator is 1,10-phenanthroline quinone.

7. The method according to claim 1, wherein the enzyme is glucose dehydrogenase or 3-hydroxybutyrate dehydrogenase.

8. The method according to claim 1, wherein one of the at least two substrates is a spacer.

9. The method according to claim 1, wherein at least a portion of the plurality of electrodes are positioned in the reaction zone.

10. The method according to claim 1, wherein the electrodes comprise carbon.

11. The method according to claim 1, wherein the biosensor comprises a strip-type identifier.

12. The method according to claim 11, wherein the strip-type identifier comprises a barcode.

13. The method according to claim 11, wherein the strip-type identifier comprises a magnetic strip.

14. The method according to claim 11, wherein the strip-type identifier comprises a notch.

15. The method according to claim 11, wherein the strip-type identifier comprises an optical detector.

16. The method according to claim 11, wherein the strip-type identifier comprises a switch.

17. The method according to claim 11, wherein the strip-type identifier comprises a circuit loop.

18. The method according to claim 1, wherein the biosensor comprises an identifier indicating a universal calibration code.

* * * * *